United States Patent [19]

Rule et al.

[11] Patent Number: 4,746,758

[45] Date of Patent: May 24, 1988

[54] PROCESSES FOR PREPARING IODINATED AROMATIC COMPOUNDS

[75] Inventors: Mark Rule; Donald W. Lane; Thomas H. Larkins, Jr.; Gerald C. Tustin, all of Kingsport, Tenn.

[73] Assignee: Eastman Kodak Company, Rochester, N.Y.

[21] Appl. No.: 912,806

[22] Filed: Sep. 29, 1986

[51] Int. Cl.$^4$ .................. C07C 17/12; C07C 17/156
[52] U.S. Cl. ................................. 570/206; 570/203
[58] Field of Search ..................... 570/206, 208, 203

[56] References Cited

U.S. PATENT DOCUMENTS

| | | | |
|---|---|---|---|
| 2,998,459 | 8/1961 | Baker et al. | 570/207 |
| 3,363,010 | 1/1968 | Schwarzenbek | 570/203 |
| 4,240,987 | 12/1980 | Martin et al. | 570/206 |

FOREIGN PATENT DOCUMENTS

| | | | |
|---|---|---|---|
| 171265 | 2/1986 | European Pat. Off. | 570/206 |
| 181790 | 5/1986 | European Pat. Off. | 570/206 |
| 183579 | 6/1986 | European Pat. Off. | 570/203 |
| 77631 | 5/1982 | Japan | 570/206 |
| 224644 | 11/1985 | Japan | 570/206 |
| 159496 | 3/1964 | U.S.S.R. | 570/206 |

OTHER PUBLICATIONS

Advanced Organic Chemistry: Reactions, Mechanisms, and Structure, March, McGraw-Hill, 1968, p. 405.

J. Org. Chem. vol. 35, No. 10, 1970, Baird et al, Halogenation with Copper(II) Halides, The Synthesis of Aryl Iodides.

Institute of Catalysis, Siberian Branch of the Academy of Sciences of the USSR, vol. 23, No. 4, pp. 992–994, Jul.–Aug., 1982; Gorodetskaya et al, Oxidative Bromination of Aromatic Compounds . . . .

Chemical Economy & Engineering Review, Apr. 1984, vol. 16, No. 4 (No. 177) Itatani: International Technological Trends in $C_1$ Chemistry.

Primary Examiner—J. E. Evans
Attorney, Agent, or Firm—Charles R. Martin

[57] ABSTRACT

This invention relates to a process for iodination of aromatic compounds in the presence of oxygen over a zeolite catalyst.

10 Claims, No Drawings

PROCESSES FOR PREPARING IODINATED AROMATIC COMPOUNDS

FIELD OF THE INVENTION

The present inventions relate to processes for iodinating aromatic compounds. In particular, the process for iodinating benzene is described. A second process for iodinating naphthalene and other condensed ring aromatics is also described. The processes utilize oxidative iodination over zeolite catalysts.

BACKGROUND OF THE INVENTION

It has long been desired to be able to derivatize aromatic compounds and in particular condensed ring aromatic compounds in commercially attractive quantities since many of these compounds possess properties which would fill long sought needs. In particular, the compound 2,6-naphthalene dicarboxylic acid or its esters is particularly desired for use in the manufacture is polyesters which would have excellent barrier properties when fabricated into films, bottles or coatings. However, known techniques for producing 2,6-naphthalene dicarboxylic acid and esters are very expensive and impractical for commercial exploitation.

DESCRIPTION OF THE PRIOR ART

Synthesis of iodobenzene starting from benzene and iodine is usually carried out in the liquid phase in the presence of an oxidative agent, preferably nitric acid. Such techniques have been described in the literature and in particular in Japanese Pat. No. 58/77830, U.S.S.R. Pat. No. 453392 and by Datta and Chatterjee in the *Journal of the American Chemical Society*, 39, 437, (1917). Other oxidative agents have also been suggested but none of these have proven to be more efficient or convenient than nitric acid. Typical of the other oxidative agents which have been suggested are iodic acid, sulfur trioxide and hydrogen peroxide as described by Butler in the *Journal of Chemical Education*, 36, 508, (1971). The use of metal halogenides to catalyze iodination has been suggested by Uemura, Noe, and Okano in the *Bulletin of Chemical Society of Japan*, 47, 147, (1974). The concept of direct iodination of benzene in the gas phase over the zeolite 13X has been suggested in Japanese Patent Publication No. 82/77631 in the absence of any oxidizing agent.

Ishida and Chono in Japanese Kokai Pat. No. 59/219241 have suggested a technique for oxyiodinating benzene over very acidic zeolite catalyst having a silica to alumina ($SiO_2:Al_2O_3$) ratio of greater than 10. In this technique benzene is reacted with iodine in the presence of oxygen to produce iodinated benzene. According to this disclosure approximately 96% of the benzene which is converted is converted to iodinated form. However, the remaining benzene is oxidized to carbon dioxide and other combustion products resulting in the loss of valuable starting material.

Other Information

Subsequent to the present invention, Paparatto and Saetti disclosed in European Patent Applications Nos. 181,790 and 183,579 techniques for the oxyiodination of benzene over zeolite catalysts. European Patent Application No. 181,790 suggests the use of ZSM-5 and ZSM-11 type zeolites which has been exchanged prior to use with the least one bivalent or trivalent cation. According to this disclosure the utilization of these zeolites in the acid or alkaline form results in a rapid decrease in catalytic activity in relatively few hours.

European Patent Application No. 183,579 suggests the utilization of X type of Y type of zeolite in non-acid form. According to Nos. 183,579 of X or Y zeolites have to be used in the form exchanged with monovalent, bivalent or trivalent cations and in particular with alkaline or rare earth cations. The techniques of Nos. 181,790 and 183,579 prepare the monoiodobenzene in selectivities in excess of 90% and only distinctly minor amounts of the diiodobenzene compounds.

Accordingly, a need exists for a process which can iodinate benzene at high conversions with substantially no oxidation of the benzene ring.

Further need exists for a process which selectively produces para-diiodobenzene with substantially no oxidation of the benzene ring.

Another need exists for a process which iodinates naphthalene preferentially at the 2-position with minimum formation of oxidation products.

A further need exists for a process which selectively produces 2,6-diiodonaphthalene with minimal oxidation of the naphthalene starting material.

BRIEF DESCRIPTION OF THE INVENTION

Accordingly one object comprises an invention to provide a process for iodination of benzene which does not utilize the strong oxidizing agents of the prior art.

Another objective comprises an invention to provide a process for the oxidative iodination of benzene in the absence of the oxidative degradation of benzene.

Yet another object comprises an invention to provide a process for the selective iodination of benzene to para-diiodobenzene.

Yet a further object comprises an invention to provide for the oxidative iodination of naphthalene wherein the 2-position is preferentially iodinated in the substantial absence of oxidation of the naphthalene.

Another objective comprises an invention for the selective iodination of naphthalene to produce 2,6-diiodonaphthalene.

These and other objects which will become apparent from the following disclosure have been achieved by the following inventions:

(1) Reacting iodine with benzene in the presence of a source of molecular oxygen and over a zeolite catalyst in base form;

(2) Reacting benzene with iodine in the presence of a source of molecular oxygen over a zeolite catalyst in base form which contains potassium, cesium, rubidium and/or barium and recovering a product containing para-diiodobenzene;

(3) Reacting naphthalene with iodine in the presence of a source of molecular oxygen over zeolite catalyst in base form wherein the base form comprises sodium, potassium, rubidium and/or cesium ions and recovering a product containing naphthalene iodinated in the 2-position;

(4) Reacting naphthalene with iodine in the presence of a source of oxygen over a zeolite catalyst in base form when at least 50% of the ion exchange cites contain potassium, rubidium or cesium and recovering a product containing 2,6-diiodonaphthalene.

DESCRIPTION OF THE PREFERRED EMBODIMENTS

Benzene

The oxidative iodination of benzene can be performed over essentially any zeolite catalyst in the non-acid form provided the pore size of the zeolite is about 6 angstroms or larger, which is the apparent size of the benzene ring. If the benzene cannot enter into the pore then little or no conversion of benzene to its iodinated form will occur. If the zeolite is in the acid form excessive combustion of the benzene occurs making the process unattractive. Hence, preferred zeolites are all in the non-acid form and all contain a pore size of about 6 angstroms or larger.

Most of the commercially available zeolites are in the sodium form. The alkali, alkaline earth and rare earth metal counter ions have all proven to yield useful zeolites for the iodination of benzene. The alkali and alkaline earth metal zeolites are preferred because there is substantially no oxidation or burning of the benzene when these are used as the counter ions. The zeolites which have been ion exchanged with rare earth metals show a higher burn rate which is generally not desired. The counter ion is easily introduced into the zeolite by simple ion exchange and is well known to those skilled in the art. This is accomplished by contacting in an aqueous medium a salt of the desired counter ion and the zeolite. The period of time with over which the contact is conducted and the number of times the ion exchange processes is preformed is dependent upon the degree of replacement which is desired. Thus, one beginning with zeolite in the sodium form may ion exchange this material with another counter ion to partially or substantially replace the sodium ion with a different counter ion. The particular counter ions which are employed has an effect upon the product composition. The utilization of sodium, lithium or magnesium counter ions tends to favor the monoiodobenzene over the diiodobenzene. This is particularly true with the high alumina content zeolites such as the X-type. When utilizing high alumina content zeolites the counter ion has a greater effect upon the product produced than when one is utilizing lower alumina content zeolites such as the Y-type. Very low alumina content zeolites such as the ZSM-5 or 11 types are even less selective even when utilizing different counter ions. The potassium, rubidium, cesium and barium counter ions favor the production of polyiodinated benzene. The comparative amounts of the di, tri and higher iodinated benzenes is largely determined by reaction time and iodine to aromatic ratio. The monoiodo isomers are favored by lower ratios and shorter contact times and the higher idodinated materials by higher ratios and longer reaction times. The preferred counter ions for the production of the polyiodinated benzenes are potassium, rubidium, cesium and barium. From a cost standpoint potassium is the most preferred counter ion for the polyiodinated benzenes although rubidium and cesium are both equally effective.

Essentially any zeolite can be utilized in this process provided greater than 10 percent of the exchangeable cations are alkali, alkaline earth or rare earth metal ions and further provided the pore size is greater than about 6 angstroms. Generally speaking reaction rate is a function of the silicon to aluminum ratio in the zeolite, since aluminum is part of the active site. It is preferred to use zeolites with a silicon (as Si) to aluminum (as Al) ratio of 10:1 or less, more particularly 5:1 or less, still more preferred are those zeolites having a silicon to aluminum ratio 3:1 or less with the most preferred type having a silicon to aluminum ratio of 1.5 or less. Particular types of zeolites which have proven to be particularly effective are the X and Y types. The Y type zeolite generally has a silicon to aluminum ratio of about 1.5 to 1 to 3:1. The X type zeolite is generally considered to have a silicon to aluminum ratio of 1:1 to 1.5:1. The X type zeolite exhibits more sensitivity to the counter ion than the Y type does. That is, the selectivity of this X type zeolite to the production of either mono, di or triiodinated benzenes can be altered more successfully through the selection of the appropriate counter ions descibed above than can the Y type. While not being bound by any particular theory, it is believed that the counter ion effects selectivity by altering the shape of the pore thereby increasing or decreasing the selectivity of the catalyst for any particular isomer as compared with the standard sodium form. As the number of cations at the active site decreases the effect of changing the shape of the pore decreases and thus selectivity decreases. Thus, when one desires to produce a particular isomer high alumina zeolites are preferred.

The total surface area of the catalyst is not critical. Obviously, the more active sites on the zeolite the greater the productivity of the process per volume of zeolite employed. Generally speaking a zeolite is prepared in a powder form and is then combined with a binder to produce a shaped catalyst. Essentially any binder can be utilized provided that the pores in the zeoliite are available or open so that the desired reaction can take place. Standard binders include alumina, silica, various types of clays and the like. The zeolite can also be used as binder-free, pressed pellets. The particular catalyst shape is a matter of choice and has not been found to be critical. Most zeolites are available commercially in the form of an extrudate and this form has been found to be useful. Utilization of this zeolite in powder form is also possible especially when a reaction is to be conducted utilizing a fluidized bed or in the liquid phase wherein the zeolite would be suspended in the liquid reactant.

The temperature at which the reaction is conducted is not critical and is largely determined by whether one desires to conduct the process in the liquid or vapor phase. The temperature need only be high enough to ensure that the zeolite is catalytically active and should be below the temperature at which benzene would undergo excessive combustion during the process. Generally speaking temperatures from 100° to 500° C. may be utilized, with temperatures of 200–400 being preferred, with the most preferred range being from 200°–350° C. In general, the utilization of lower temperatures tends to favor the selectivity to the para-diodobenzene although the catalyst activity as measured by percent conversion decreases with decreasing temperature.

The pressure at which the process is conducted is not critical and can range from subatmospheric to superatmospheric. The utilization of elevated pressures in the gas phase process may be preferred so as to minimize equipment size. In general, pressures from atmospheric to 600 psig have been proven satisfactory.

The molecular oxygen can be introduced as pure oxygen, air or oxygen diluted with any other inert material such as carbon dioxide or water vapor. Essentially oxygen from any convenient source may be utilized. The purpose of the oxygen is to regenerate the active site on the zeolite to its active form once the iodination reaction has occurred. Thus the amount of oxygen present during the reaction is not critical. However, it is preferred that at least one-half mole of oxygen be used for every mole of iodine. The molar ratio of iodine to benzene which is to be reacted is largely determined whether one desires to produce a monoiodobenzene product or a polyiodinated benzene product. Stoichiometrically, one-half mole of iodine reacts with one mole of benzene to produce the monoiodinated form. Similarly, on a stoichiometric basis one mole of iodine is required to convert one mole of benzene to the diiodinated form. Greater or lesser quantities of iodine can be utilized as the artisan may desire. The utilization of excess quantities of iodine result in a product which is contaminated with unreacted iodine and thus will contain a high color level. When all of the iodine is reacted a colorless product is obtained. In general, it is desired to run the process to obtain a close to 100% conversion of the iodine as possible so as to simplify the purification steps and the recovery of any unreacted iodine. Suggested mole ratios of benzene to iodine to oxygen are from about 1:0.5:0.25 to about 1:2:3. However, other ratios may be utilized as desired. The molar ratio of iodine to benzene is not critical.

With regard to this invention we use the term "iodine" in a broader sense than merely the compound $I_2$ and regard the term as meaning any source of iodine atoms that will permit practice of the invention. Elemental iodine is of course such a source of iodine but the iodine can be provided by hydroiodic acid or an alkyl iodide. Mixtures of these can also be used.

It is anticipated that the present process would be carried out continuously by the continuous addition of iodine, oxygen and benzene to the reactor, however, the process can also be carried out on batch or semibatch process as desired.

The spaced velocity of the process is not critical and may be readily selected by the artisan. Gas hourly space velicities between 10 and 10,000, preferably between 100 and 2,000 liters per hour or reagents per liter of active zeolite, have proven satisfactory.

The catalyst has proven to have an extremely long life and degrades only slowly with time. The degradation of the catalyst is believed to be caused by the combustion of very small quantities of benzene which deposits small quantities of carbon in the active sites thereby degrading the catalyst activity. When the reaction conditions are selected such that no benzene is oxidized, the life of the catalyst is essentially indefinite. However, when the catalyst become deactivated reactivation is simple. An excellent regeneration technique comprises passing air or oxygen over the catalyst for several hours at a temperature above 400° C., although higher or lower temperatures are proven equally satisfactory. The temperatures need only be high enough so as to ensure combustion of the carbon deposit on the catalyst. When pure oxygen is employed lower temperatures can be utilized, while when air is employed temperatures of about 400° C. have proven satisfactory.

The iodinated benzene compounds produced by the process of this invention are useful as intermediates. Monoiodobenzene can be hydrolyzed to phenol which can be used to prepare resins according to methods well known in the art. Diiodobenzene can be aminolyzed to diamines useful for preparing polyamide resins according to known methods.

Naphthalene

It is well known that naphthalene is more susceptible to oxidation than is benzene. Thus, it was quite surprising to find conditions under which the naphthalene could be oxyiodinated with substantially no oxidation of the naphthalene ring. Still more surprising was the discovery that the oxyiodination strongly favored the 2-position on the naphthalene ring. Prior conventional liquid iodination techniques for iodinating naphthalene, such as the utilization of iodine and nitric acid or other strong oxidants has preferentially produced iodination in the 1-position; greater than 99% of the product was iodinated in the 1 or alpha position. The present technique preferentially iodinates the 2-position, with the minimum iodination at the 2 or beta position being at least 50%. This ability to selectively iodonate the 2-position is of extreme importance since it is the 2,6-naphthalene dicarboxylate (a beta-beta dicarboxylate) which is of principle commercial interest.

In order to successfully iodinate naphthalene, it is necessary that the zeolite have been ion exchanged with sodium, potassium, rubidium and/or cesium, more preferably with potassium, rubidium or cesium. It has been found that when the zeolite is ion exchanged with lithium, calcium, strontium or barium or rare earth metals that the naphthalene is oxidized by the oxygen present in the gas stream to a high degree. It was surprising to discover that with potassium, rubidium and cesium the degree of naphthalene oxidation is significantly less than 1% of the naphthalene converted. That is, essentially no oxidation of the naphthalene occurs with these counter ions. When the zeolite is essentially in the sodium form, oxidation of the naphthalene occurs but to a lesser extent than with lithium, calcium, strontium, barium and rare earth metal counter ions. In view of the higher oxidation rate obtained when the zeolite is in the sodium form, it is preferred that the zeolite be ion exchanged with potassium, rubidium and cesium such that at least 50% of the sodium ions are replaced by one or more of potassium, rubidium or cesium. Once the content of potassium, rubidium or cesium exceeds about 75% of the ion exchange sites the oxidation rate for napthalene drops to well below 1% of the naphthalene converted. It is preferred that as large a percentage of the ion exchange sites contain potassium, rubidium and/or cesium as is practical. However, such high degree of conversion is not necessary for the successful practice of the invention. Once more than 50% of the ion exchange groups contains potassium, rubidium or cesium excellent results are obtained.

The type of zeolite which is utilized is not critical so long as greater than 10 percent of the exchangable cations are alkali, alkaline earth or rare earth metals and the pore size is greater than about 6 angstroms. It is most preferred to utilize zeolite catalysts which favor the production of 2,6 isomer and limit production of the 2,7 isomer. The desired 2,6 isomer can easily be separated from monoiodinated naphthalenes, triiodinated naphthalenes and isomers other than the 2,7 by simple solvent extraction or cyrstallization. However, separation of the 2,6 isomer from the 2,7 isomer is difficult and thus conditions which limit the production of the 2,7 isomer are to be preferred. Since reactivity and selectivity is generally, with a few exceptions, a function of the silicon to aluminum ratio it is preferred that this ratio be less than 10:1, more preferably less than about 5:1, still more preferably less than about 3:1 and most preferably less than about 1.5:1 (as Si:Al). Zeolites having a silicon to aluminum ratio from about 1.5:1 to about 3:1 are available as the Y type which those having a silicon to aluminum ratio of 1:1 to about 1.5:1 are commercially available as the X type. The 13X type zeolite is preferred. The most preferred zeolite is the 13X type which has been ion exchanged with potassium, rubidium or cesium. The ratio of 2,6- to 2,7-diiodonaphthalene generally increases with increasing amounts of these ions.

The reaction conditions are chosen such that the naphthalene is a liquid or gas under the reaction conditions. Thus, the temperature and pressure conditions selected are such that the naphthalene is in either the liquid or vapor state or both. It is possible to conduct the process under reaction conditions where the naphthalene is constantly vaporizing and condensing, i.e., at or near its boiling point. The particular temperatures employed may range from a low of 100° C. to a high of 400° C. More preferably from 150°–400° C. and most preferably from about 200°–350° C. In general, lower temperatures favor the production of the 2,6 isomer over the 2,7 isomer and for this reason are to be preferred. However, the use of lower temperatures does result in reduced catalytic activity and reduced conversion.

The total surface area of the catalyst is not critical. Obviously, the more active sites on the zeolite the greater the productivity of the process per unit volume of zeolite employed. It is essential only that the pores be exposed so that the desired reaction can occur. The zeolites may be bound using a conventional binding agent such as alumina, silica, clays and the like to form large granules or extruded shapes or may be utilized in the form of fine powders. The zeolites can also be used as binder free, pressed pellets. A particular shape or form of the zeolite being a matter of individual choice. The conventional extrudate shape which is commercially available has been found to be satisfactory but other shapes or sizes may be utilized depending upon the reactor and process conditions. When utilizing a fluidized bed one generally will utilize a smaller particle catalyst particle size than when utilizing a fixed bed. When the process is conducted in the liquid phase, the zeolite may be suspended in the liquid phase in the form of fine particles or the liquid may be passed over and/or through a bed of the catalyst, the particular technique being a matter of individual preference.

The molecular oxygen can be introduced as pure oxygen, air or oxygen diluted with any other inert material, such as water or carbon dioxide. The purpose of the oxygen is to regenerate the active site on the zeolite to its active form once the iodination reaction has occurred. Thus the amount of oxygen present during the reaction is not critical. However, it is preferred that at least one-half mole of oxygen be used for every mole of iodine. The molar ratio of iodine to naphthalene which is to be reacted is largely determined whether one desires to produce a moniodonaphthalene product or a polyiodinated naphthalene product. Stoichiometrically, one-half mole of iodine reacts with one mole of naphthalene to produce the monoiodinated form. Similarly, on a stoichiometric basis one mole of iodine is required to convert one more of naphthalene to the diiodinated form. Greater or lesser quantities of iodine can be utilized as the artisan may desire. The utilization of excess quantities of iodine result in a product which is contaminated with unreacted iodine and thus will contain a high color level. When all of the iodine is reacted a colorless product is obtained. In general, it is desired to run the process to obtain as close to 100% conversion of the iodine as possible so as to simplify the purification steps and the recovery of any unreacted iodine. Suggested mole ratios of naphthalene to oxygen are from about 1:0.5:0.25 to about 1:2:3. However, other ratios may be utilized as desired. The molar ratio of iodine to naphthalene is not critical.

The oxygen utilized in the process may come from any suitable source including air, pure oxygen or oxygen diluted with other inert gas.

The space velocity of the process is not critical and may be readily selected by the artisan. Gas hourly spaced velocities between 10 and 10,000, preferably between 1,000 and 2,000 liters per hour of reactants per liter of active zeolite, have proven satisfactory.

With regard to this invention we use the term "iodine" in a broader sense than merely the compound $I_2$ and regard the term as meaning any source of iodine atoms that will permit practice of the invention. Elemental iodine is of course such a source of iodine but the iodine can be provided by hydroiodic acid or as an alkyl iodide. Mixtures of these can also be used.

In addition to naphthalene, other condensed ring aromatics can also be iodinated by the present technique. In particular, condensed ring aromatics such as anthracene and the like can be treated under substantially the same conditions as naphthalene. When utilizing such higher condensed ring aromatics, the process conditions can be adjusted so that the reaction occurs in either the liquid, gas phase or both phases which may require a somewhat higher minimum temperature than is required for naphthalene.

The iodinated naphthalene compounds produced by the process of this invention are useful as intermediates. 2-Iodonaphthalene can be hydrolyzed to 2-naphthol which can be used to prepare dyes in accordance with known methods. 2,6-Diidonaphthalene can be aminolyzed to the corresponding diamine which are useful in preparation of condensation polymers in accordance with known technology.

Ion Exchanging Zeolites

The process of ion exchanging zeolite ctalysts to introduce the desired counter ion is well known in the art. In general, these techniques involve treating the zeolite (which is typically in the sodium form although other forms are commercially available) with the fluid medium containing the desired counter ion. In carrying out the treatment with fluid medium, the procedure employed comprises contacting the zeolite with desired fluid medium or media until such time as the ions originally present in the zeolite are replaced to the desired extent. Repeated use of fresh solutions of the entering ion is of value to secure more complete exchange. Effective treatment with the fluid medium to obtain the modified zeolite having high catalytic activity will vary with the duration of the treatment and the temperature at which it is carried out and the number of exchanges. Elevated temperatures tend to hasten the speed of treatment and the degree of exchange varies directly with the concentration of the ions in the fluid medium. In general, temperatures of from below ambient room temperature of 24° C. up to temperatures below the decomposition temperature of the zeolite may be employed. Following the treatment, the treated zeolite is washed with water, preferably distilled, until the effluent wash water is essentially free of ions. The zeolite material is thereafter analyzed for metallic ion contents by conventional techniques. The ion substituted zeolite is then dried.

The fluid treatment of the zeolite may be accomplished batchwise or continuously under atmospheric, substmospheric or superatmospheric pressure. A solution of the ions in the form of molten material, aqueous or non-aqueous solution may be passed through a fixed bed of zeolites. If desired, hydrothermal or corresponding non-aqueous treatment with polar solvents may be effected by introducing the zeolite and fluid medium into a closed vessel maintained under autogeneous pressure.

The alkali metal or alkaline earth metal cations can be obtained from a wide variety of organic and inorganic salts. Suitable salts include the chlorides, sulfates, nitrates, acetates, bromides, carbonates, oxides, and the like of the desired metal.

The following examples are presented to illustrate the present inventions but are not intended to anyway limit the scope of the invention which is defined by the appended claims. Under the conditions employed each mole percentage of carbon dioxide in the vent gas correlates with about one-half mole percentage benzene or naphthalene combusted.

EXAMPLE 1

About 100 grams of an extruded pelleted base sodium form of aluminosilicate catalyst (Na-13X) (pellets about $\frac{1}{8}''$ by $\frac{1}{4}''$) containing about 20 percent by weight clay binder is added to a solution of 45 grams potassium chloride and 0.25 grams potassium hydroxide in 200 ml water and heated on a steam bath for one hour to exchange the sodium ions for potassium ions. The solution is decanted from the treated aluminosilicate and the treated aluminosilicate washed with a liter of distilled water. This treatment of the aluminosilicate catalyst is repeated three more additional times. After the fourth treatment the catalyst is dried on a steam bath. The dried catalyst is then calculated for four hours at 400° C. After calcination, the potassium exchanged aluminosilicate catalyst (K-13X) is washed once with distilled water and dried on a steam bath.

EXAMPLE 2

About 100 g of binder-free 13X powder is placed in a large evaporating dish. The evaporating dish is placed in desicator saturated with water vapor and left in the desicator until its weight is constant. The hydrated zeolite is slurried in a solution of 272.1 g rubidium chloride in 1000 ml distilled water. The slurry is stirred at boiling for two hours and then the hot slurry is filtered and washed with 1000 ml distilled water. The exchange procedure is repeated two more times. After the final exchange the zeolite is washed with distilled water until the washings do not form a precipitate with aqueous silver nitrate solution. The exchange zeolite is then dried at 100° C. until a free-flowing powder is obtained. The power is pelletized with a hydraulic press and the pellets are sized to pass an 8-mesh screen.

EXAMPLES 3-9

The invention is practiced following the general procedure described in Examples 1 and 2 using benzene. The ratio of oxygen to benzene to $HI_3$ was 2.5:2.3:0.8, the iodine being delivered as $HI_3$. Various catalysts, reaction temperatures and space velocities were used resulting in various percentage conversion of benzene and composition of products.

| Example Number | Catalyst | Reaction Temp., °C. | Gas Hourly Space Vel., $hr^{-1}$ | Benzene Conversion, % | Iodobenzenes Space Time Yields, $g\ l^{-1}\ hr^{-1}$ | | | | Vent Gas Anal. | |
|---|---|---|---|---|---|---|---|---|---|---|
| | | | | | mono | meta | para | ortho | $CO_2$, % | $O_2$, % |
| 3 | Na—X | 340 | 1260 | 98 | 188 | 41 | 91 | 11 | 0.25 | 8.9 |
| 4 | K—X | 339 | 1260 | 15 | 120 | 25 | 63 | 0 | 0.34 | 11.0 |
| 5 | Li—X | 340 | 1265 | 79 | 291 | 80 | 85 | 23 | 0.32 | 9.2 |
| 6 | Cs—X | 343 | 1280 | 54 | 174 | 59 | 73 | 0 | 0.41 | 9.2 |
| 7 | Mg—X | 334 | 1280 | 62 | 298 | 50 | 47 | 17 | 0.17 | 10.6 |
| 8 | Ba—X | 345 | 1290 | 44 | 187 | 46 | 126 | 11 | 1.30 | 9.1 |
| 9 | Na—Y | 350 | 1240 | 10 | 100 | 12 | 40 | 7 | 3.57 | 12.4 |

EXAMPLE 10

A vertical tubular Hastelloy reactor about 1 inch in diameter was packed with 200 cc of potassium exchanged aluminosilicate catalyst as prepared in Example 1. The reactor was positioned in an electric furnace and heated to 300° C. A mixture of benzene, iodine, and air was passed through the reactor at 15 psia a rate of 30 ml/hr benzene, 14.42 g/hr iodine, and 150 ml/minute air (STP). After 21 hours on-line, the product composition was 34.0 wt % benzene, 39.9 wt % iodobenzene, 5.5 wt % m-diiodobenzene, 14.9 wt % p-diiodobenzene, and 0.8 wt % o-diiodobenzene. The vent gas contained 0.83% $CO_2$. After 800 hours on-line the product composition was 36.2 wt % benzene, 42.1 wt/% iodobenzene, 6.1 wt % m-iodobenzene, 17.9 wt % p-diiodobenzene, and 0.83% $CO_2$ in the vent gas. Iodine consumption throughout the experiment was 99.9%.

EXAMPLE 11

Example 10 was repeated except the reaction pressure was 45 psia and 90 ml/hr benzene, 43.4 g/hr iodine and 450 ml/min air (STP) were fed across the catalyst. The product composition was 33.1 wt % benzene, 41.5 wt % iodobenzene, 6.4 wt % diiodobenzene. The vent gas composition was 91.7% $N_2$, 7.4% $O_2$ and 0.89% $CO_2$. Iodine consumption was 99.8%,.

EXAMPLES 12-21

The invention is practiced following the general procedure described in Examples 3-9 using naphthalene. Various catalysts, mole ratios, reaction temperatures and space velocities are used resulting in various percentage conversion of naphthalene and composition of products. Details of these examples as presented below.

| Example Number | Zeolite Catalyst | Molar Ratio | | | Reaction Temp., °C. | Gas Hourly Space Vel., hr$^{-1}$ | Naph. Conversion, % | Space Time Yield, g l$^{-1}$ hr.$^{-1}$ | | | | Ratio 2,6/2,7 | Vent Gas | |
|---|---|---|---|---|---|---|---|---|---|---|---|---|---|---|
| | | O$_2$ | Naph. | I$_2$ | | | | 2-iodo | i-iodo | Other diiodo | 2,6 & 2,7-diiodo | | CO$_2$, % | O$_2$, % |
| 12 | Rb—X | 1.0 | 1.0 | .47 | 322 | 1230 | 57 | 225 | 142 | 45 | 242 | 71/29 | .4 | 12.2 |
| 13 | K—X | 1.0 | 1.0 | .50 | 337 | 1220 | 74 | 344 | 110 | 69 | 273 | 58/42 | 1.3 | 10.4 |
| 14 | Cs—X | 1.0 | 1.0 | .48 | 325 | 1230 | 66 | 277 | 144 | 99 | 245 | 57/43 | 1.9 | 9.9 |
| 15 | Na—X | 1.1 | 1.0 | .49 | 328 | 880 | 61 | 228 | 72 | 35 | 92 | 49/51 | 3.7 | 9.5 |
| 16 | Zeolite L | 1.0 | 1.0 | .43 | 331 | 860 | 20 | 40 | 93 | 3 | 1 | 42/58 | .3 | 12.0 |
| 17 | Ba—X | 1.2 | 1.0 | .41 | 321 | 410 | 1 | 3 | 0 | 0 | 0 | — | 5.2 | 7.7 |
| 18 | Ca—X | 1.1 | 1.0 | .49 | 321 | 780 | 4 | 22 | 0 | 0 | 0 | — | 3.2 | 9.7 |
| 19 | Sr—X | 1.2 | 1.0 | .42 | 324 | 440 | 7 | 21 | 0 | 0 | 0 | — | 14.4 | .9 |
| 20 | Li—X | 1.3 | 1.0 | .47 | 327 | 390 | 8 | 6 | 14 | 0 | 0 | — | 8.9 | 5.5 |
| 21 | Mg—X | 1.0 | 1.0 | .47 | 321 | 1230 | 8 | 20 | 39 | 0 | 0 | — | .4 | 14.3 |

As can be seen from the foregoing examples and comparative examples, the results obtained when utilizing naphthalene as a starting material were not predictable from the results obtained for benzene. It would be expected that if naphthalene were substituted for benzene a greater mole percentage of naphthalene would be combusted. It was surpsing, however, that oxidation of naphthalene with selected catalysts was not substantially greater than benzene. It is generally recognized that naphthalene is more highly oxidizable than is benzene under the comparable conditions. Second, it was even more surprising to discover that the iodination of naphthalene would occur predominantly at the 2-position when iodination at the 1-position is expected from the prior art where over 99% iodination at the 1-position is obtained.

Obviously, numerous modifications and variations of the present invention are possible in light of the above teachings. It is therefore to be understood that within the scope of the appended claims, the invention may be practiced otherwise than as specifically described herein.

We claim:

1. A method for iodinating naphthalene in the 2-position by reacting napththalene with a source of iodine in the presence of a source of molecular oxygen over a zeolite catalyst containing sodium, potassium, rubidium or cesium ions.

2. The process of claim 1, wherein at least 50% of the ion exchange sites in the zeolite contain potassium, rubidium, cesium ions or mixtures thereof.

3. The process of claim 1, wherein the pore size of the zeolite is greater than about 6 angstroms.

4. The method of claim 1, wherein the ratio of silicon to aluminum in the zeolite is less than 10:1.

5. The method of claim 1, wherein the ratio of silicon to aluminum in the zeolite is less than about 5:1.

6. The method of claim 1, wherein the ratio of silicon to aluminum in the zeolite is less than 3:1.

7. The method of claim 1, wherein the ratio of silicon to aluminum is between about 1:1 and 1.5:1.

8. The method of claim 1, wherein the zeolite is 13X type zeolite which has been ion exchanged with potassium, rubidium, cesium ions or mixtures thereof.

9. The process of claim 1, wherein the temperature is betwen 200° and 350° C.

10. The process for the iodination of condensed ring aromatic compounds by reacting said condensed ring aromatic compound with a source of iodine in the presence of a source of oxygen over a zeolite catalyst containing sodium, potassium, rubidium, cesium ions or mixtures thereof.

* * * * *